(12) United States Patent
Ramsbottom et al.

(10) Patent No.: US 10,310,250 B2
(45) Date of Patent: Jun. 4, 2019

(54) METHOD AND APPARATUS FOR INSPECTION OF MOVING PARTS IN ROTARY SYSTEM

(71) Applicant: KEYMED (MEDICAL & INDUSTRIAL EQUIPMENT) LTD., Essex (GB)

(72) Inventors: Andrew Paul Ramsbottom, Essex (GB); Gareth Willerton Sykes, Essex (GB)

(73) Assignee: KEYMED (MEDICAL & INDUSTRIAL EQUIPMENT) LTD. (GB)

( * ) Notice: Subject to any disclaimer, the term of this patent is extended or adjusted under 35 U.S.C. 154(b) by 0 days.

(21) Appl. No.: 15/746,481

(22) PCT Filed: Jul. 22, 2016

(86) PCT No.: PCT/GB2016/052233
§ 371 (c)(1),
(2) Date: Jan. 22, 2018

(87) PCT Pub. No.: WO2017/017422
PCT Pub. Date: Feb. 2, 2017

(65) Prior Publication Data
US 2018/0210189 A1    Jul. 26, 2018

(30) Foreign Application Priority Data

Jul. 24, 2015   (GB) .................................. 1513063.6

(51) Int. Cl.
G02B 23/24      (2006.01)
G01N 21/954     (2006.01)
(Continued)

(52) U.S. Cl.
CPC ....... G02B 23/2484 (2013.01); G01N 21/954 (2013.01); H04N 5/2258 (2013.01);
(Continued)

(58) Field of Classification Search
CPC ............. G02B 23/2484; G01N 21/954; G01N 2021/1774; G01N 2021/9546; H04N 5/2258; H04N 7/183; H04N 2005/2255
See application file for complete search history.

(56) References Cited

U.S. PATENT DOCUMENTS 4,532,544 A     7/1985   Federau
2002/0067845 A1 6/2002   Griffis
(Continued)

FOREIGN PATENT DOCUMENTS

| | | |
|---|---|---|
| EP | 1179801 B1 | 8/2007 |
| EP | 2778740 A3 | 11/2014 |
| WO | 0194966 A2 | 12/2001 |

OTHER PUBLICATIONS

International Search Report PCT/GB2016/052233, dated Sep. 26, 2016.
(Continued)

*Primary Examiner* — Thai Q Tran
*Assistant Examiner* — Sunghyoun Park
(74) *Attorney, Agent, or Firm* — Luedeka Neely Group, PC

(57) ABSTRACT

A method for capturing an image of a moving object in a rotary system, for example, an image of a rotating blade in a gas turbine, uses an endoscope to form an image of a moving object. One-dimensional line images are captured with a line scan image sensor which is oriented to lie orthogonal to the direction of movement of the image of the moving object past the image sensor. Successive line images are combined to form a composite two-dimensional image
(Continued)

of the moving object. A second image may be detected using a second line scan image sensor oriented orthogonal with respect to the direction of movement of the image, to the first line scan image sensor.

6 Claims, 3 Drawing Sheets

(51) Int. Cl.
*H04N 5/225* (2006.01)
*H04N 7/18* (2006.01)
*G01N 21/17* (2006.01)

(52) U.S. Cl.
CPC ..... *H04N 7/183* (2013.01); *G01N 2021/1774* (2013.01); *G01N 2021/9546* (2013.01); *H04N 2005/2255* (2013.01)

(56) References Cited

U.S. PATENT DOCUMENTS

| | | | |
|---|---|---|---|
| 2007/0132840 A1* | 6/2007 | Konomura | G01N 21/954 348/65 |
| 2012/0162192 A1* | 6/2012 | Wang | F01D 11/14 345/419 |
| 2013/0113915 A1* | 5/2013 | Scheid | F01D 17/02 348/82 |
| 2014/0267678 A1* | 9/2014 | Kobayashi | G02B 23/2484 348/82 |
| 2015/0002841 A1* | 1/2015 | Konomura | F01D 5/12 356/241.6 |
| 2015/0022655 A1 | 1/2015 | Ruhge | |
| 2015/0168263 A1* | 6/2015 | Mueller | F01D 21/003 348/82 |
| 2016/0178532 A1* | 6/2016 | Lim | G01N 21/8851 348/46 |

OTHER PUBLICATIONS

Patents Act 1977: Search Report under Section 17, GB1513063.6, date of search Jan. 15, 2016.

* cited by examiner $F_b$ = Field of view of borescope
$F_l$ = Equivalent field of view of line scan image $$F_l = \sqrt{2} \cdot F_b$$

METHOD AND APPARATUS FOR INSPECTION OF MOVING PARTS IN ROTARY SYSTEM

CROSS-REFERENCE TO RELATED APPLICATION

This application claims priority under all applicable statutes, and is a U.S. National phase (37 U.S.C. Section 371) of International Application PCT/GB2016/052233, filed Jul. 22, 2016, and entitled METHOD AND APPARATUS FOR INSPECTION OF MOVING PARTS IN ROTARY SYSTEM, which claims priority to GB 1513063.6, filed Jul. 24, 2015, incorporated herein by reference in their entireties.

The present invention relates to a method and apparatus for image capture and inspection of continuously moving parts in a rotary system.

Rotary machines with continuously rotating parts are commonplace in many applications. Prime examples are gas turbines and compressors used, for example, in aircraft, marine and military tank propulsion and electrical power generation. These machines typically consist of one or more stages of rotating discs with aerofoil-shaped blades mounted around their circumference.

In many such systems, the integrity of the rotating parts is a safety critical issue. There is a need to regularly inspect the moving parts in order to determine their condition, integrity and effectiveness and identify the need for preventive maintenance. An aircraft engine, for example, may have a requirement for inspection of the compressor and turbine blades every 300 flying hours. The inspection may be looking for cracks, dents, nicks, tears, erosion, blocked cooling holes and material or coating damage.

In most applications, the high capital cost of such equipment, and the need to maximise its use, means there is a significant benefit in being able to inspect the systems in situ, for example, in the case of an aircraft engine, while it is still mounted on the aircraft wing. Furthermore, reducing the time taken for such inspections and therefore the system downtime usually carries significant financial and logistical benefits.

The conventional method for inspecting such parts is to use a rigid industrial endoscope (sometimes called a borescope) or a flexible video scope which is inserted into the engine through small inspection ports. A typical gas turbine engine for aircraft propulsion may have ten or more compressor stages and five or more turbine stages, each with between 20 and 60 individual blades. Current inspection methods are largely manual operations, where a skilled technician will use the endoscope to inspect each blade on each stage. The engine is rotationally indexed, either manually or by means of a specialist engine turning tool, to position each blade relative to the scope at a suitable position to enable the inspection. The operator may then perform a visual inspection and/or capture an image of the blade by means of a camera attached to or integral with the scope, for further analysis, measurement or archiving and reference purposes. Given the number of stages and blades and the need to accurately step and repeat the engine rotation and image capture, this process may take a considerable time, typically a whole day for a modern gas turbine engine. This is expensive in terms of system downtime.

The present invention provides a method for capturing an image of a moving object in a rotary system, comprising using an endoscope to form an image of a moving object, capturing 1-dimensional line images with a line scan image sensor which is oriented to lie orthogonal to the direction of movement of the image of the moving object past the image sensor, and combining successive line images obtained by the image sensor to form a composite 2-dimensional image of the moving object.

Preferably, the endoscope comprises an elongate shaft with a proximal end and a distal end and an optical system operable to form an image of an object adjacent to the distal end and transmit the image to the proximal end, the method further comprising arranging the image sensor at the proximal end to receive the image from the optical system.

The method may further comprise detecting a second image using a second line scan image sensor oriented orthogonal, with respect to the direction of movement of the image, to the first line scan image sensor.

This may be achieved by providing a beam splitter to transmit the image obtained by the endoscope to both first and second image sensors.

Alternatively, it may be achieved by providing a second endoscope associated with the second image sensor and positioning the second endoscope adjacent a second moving object in the rotary system which is mechanically linked to the first moving object.

In either case, using the image from the second image sensor may be used to correct the composite image obtained by the first image sensor in order to compensate for variations in the speed of movement of the first object.

Alternatively, the method may comprise using a signal derived from a moving image feature on the second image sensor to trigger the line image capture by the first image sensor.

The present invention also provides apparatus for capturing an image of a continuously moving object in a rotary system, comprising at least one endoscope to form an image of a moving object, at least one line scan image sensor oriented orthogonal to the direction of movement of the image of the object past the image sensor to capture 1-dimensional line images, and a processor to combine the line images captured by the image sensor to form a composite 2-dimensional image of the object.

The endoscope may comprise an elongate shaft with a proximal end and a distal end and an optical system operable to form an image of an object adjacent the distal end and transmit the image to the proximal end and the image sensor is arranged at the proximal end of the shaft.

The apparatus may further comprise a second line scan image sensor arranged to capture a second image and oriented orthogonal, with respect to the direction of movement of the image, to the first image sensor.

The endoscope may comprise a beam splitter operable to transmit the image captured by the endoscope to both the first and second image sensors.

Alternatively, the apparatus may further comprise a second endoscope, wherein the first endoscope is associated with the first image sensor and the second endoscope is associated with the second image sensor and the endoscopes are arranged to view mechanically linked objects in the rotary system.

The present invention will now be described in detail, by way of example only, with reference to the accompanying drawings in which.

Figure 1:
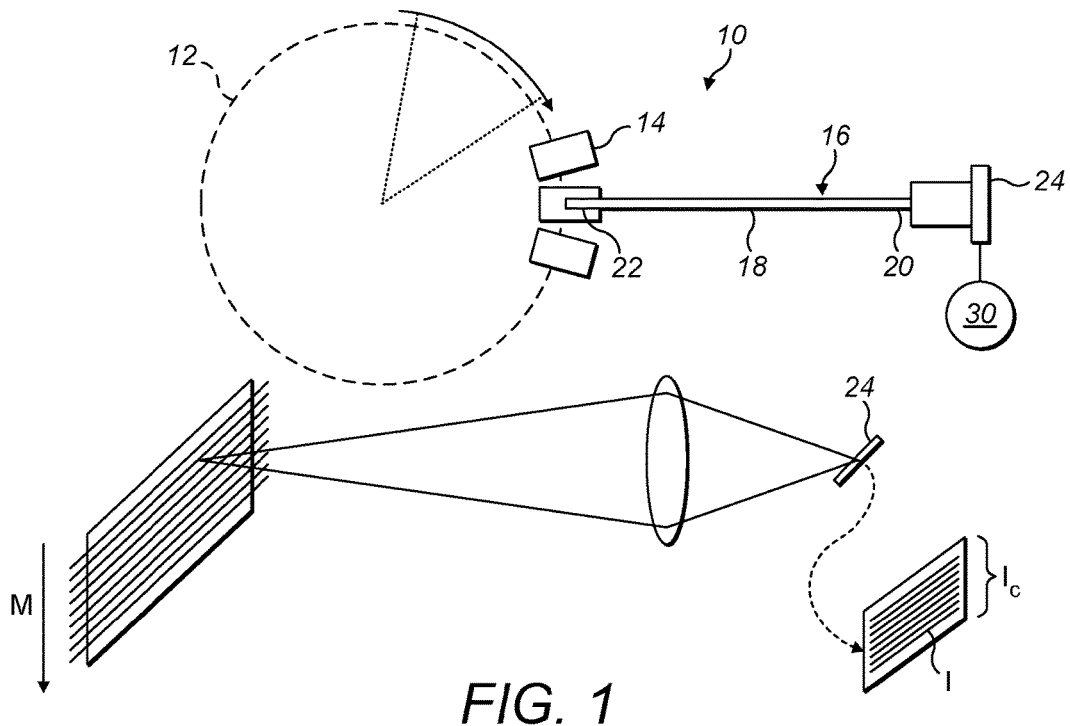
FIG. 1 is a schematic diagram illustrating the apparatus of the present invention and representing the image capture process.

The apparatus 10 of the present invention is shown schematically in FIG. 1. The rotary system being inspected is indicated by a dotted circle which represents, for example, a compressor or turbine disc 12 of a gas turbine engine. A plurality of blades 14 (only some of which are shown) are mounted around the circumference of the disc 12. An endoscope 16 is positioned extending radially with respect to the disc 12. It is normally inserted into the engine via an inspection port so that the distal end of the endoscope 16 is adjacent each blade 14 in turn as the disc 12 rotates.

As used herein, the term "endoscope" is intended to cover devices referred to as borescopes, video scopes, flexi scopes or any similar terms which refer to suitable devices for capturing an image at a remote or inaccessible location and transmitting the image to another location so that it can be viewed on a monitor and/or processed, manipulated and saved by a computer. Such devices may be rigid or flexible.

The endoscope 16 has an elongate shaft 18 with proximal and distal ends 20, 22. In a conventional manner, the shaft 18 has a viewing window (not shown) at the distal end 22 and may enclose an optical system (with lenses, optical fibres, etc.), to capture an image of an object adjacent to the distal end 22 and convey the image to the proximal end 20 where it is received by an electronic image sensor 24. Alternatively, the endoscope 16 may have an image sensor 24 at the distal end 22 and means to convey the captured image electronically to the proximal end 20. In either case, information from the image sensor 24 is transmitted to a processor 30 which is operable to store, manipulate and display the image.

In the present invention, the image sensor 24 comprises a line scan camera which has a single line of sensor pixels. Thus, as illustrated in the lower part of FIG. 1, each image I captured by the sensor 24 consists of a single line and a complete image Ic is built up by making successive single line scans while the object moves in a perpendicular direction indicated by the arrow M past the line of sensor pixels.

Typically, line scanning is used in situations in which the object being viewed is moving at constant speed past a stationary sensor, for example, on a production line or for inspecting a continuous web of paper, glass or fabric, or when the imaging array is moved relative to the object, for example, in fax and scanning machines. Line scanning has a number of advantages for imaging moving objects. In particular, it avoids problems of motion blur or image smear. The dynamic range (i.e. the range of light levels which the sensor can cope with) can be much higher than alternative image capture methods. There is a high "fill-factor" and therefore higher sensitivity with a line scanner as opposed to an area pixel array, because the full area of the pixel is available for sensing. Line scanning also eliminates frame overlaps which are required to build a seamless image with area sensors. Frame overlaps represent redundant data that uses up precious processing bandwidth, particularly in high speed, high resolution applications. Line scanning also offers more cost-effective implementations of high spatial resolution image capture.

In the present invention, the endoscope 16 is arranged such that its direction of view is towards the blades 14. As the disc 12 rotates, each blade 14 passes the distal end of the scope 16. Due to the small size of the image capture part of the endoscope 16 relative to the blade 14, the blade 14 effectively moves past it in a straight line, tangential to the disc 12 circumference, past the endoscope viewing window. The image sensor 24 is arranged so that the line of pixels is orthogonal to the direction of movement of the blades 14.

As the disc 12 rotates, the line scan sensor 24 repeatedly captures individual line images I which are built-up by the processor to form a full frame complete image Ic of each blade 14 on the entire stage. The images can then be inspected, either visually by a trained operator or automatically by a computer system to detect any issues with the blade.

Figure 2:
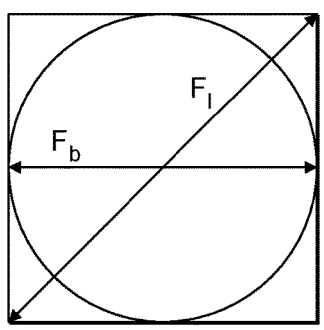
FIG. 2 is a diagram illustrating field of view.

A further advantage of this system over conventional endoscope imaging is that there is an effective increase in the field of view, with no consequent increase in field dependent aberrations. This is illustrated in FIG. 2 in which the circle with diameter $F_b$ represents the field of view of a conventional endoscope and the diagonal arrow $F_l$ shows the equivalent field of view of a line scan image. Specifically, $F_l = \sqrt{2} \times F_b$.

Figure 3:
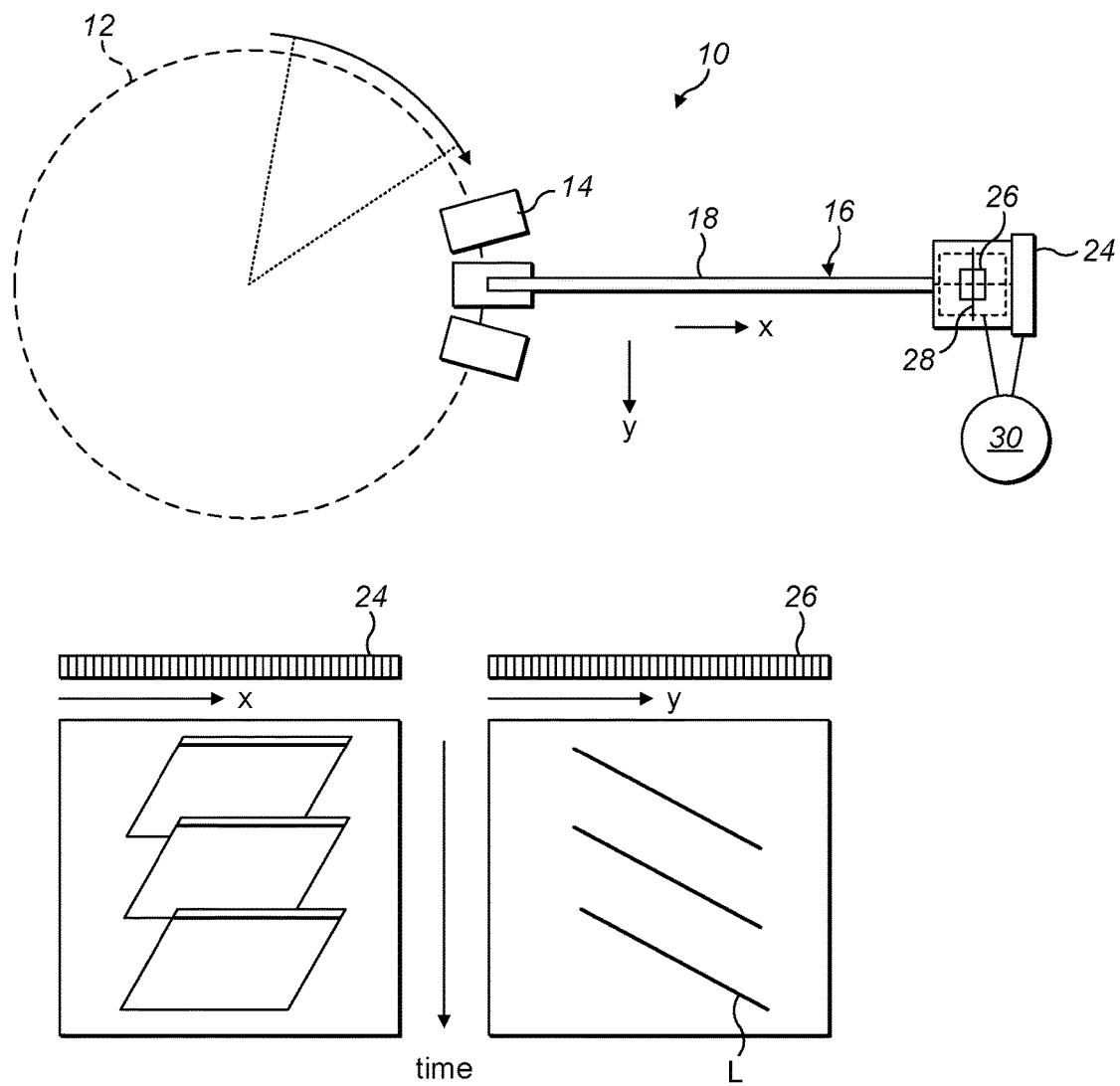
FIG. 3 is a schematic diagram of a further embodiment of the invention.

A further embodiment of the present invention is illustrated in FIG. 3. This uses a second line scan camera to compensate for any variations which may occur in the speed of rotation of each blade 14. In this embodiment, a second line scan image sensor 26 is arranged with its line of pixels orthogonal to the line of pixels of the first line scan image sensor 24. As shown in FIG. 3, this may be achieved by using a single endoscope 16 with a beam splitter device 28 at the proximal end 20. This transmits the image obtained by the endoscope 16 to both image sensors 24, 26.

With this arrangement, whilst the first image sensor 24 builds up a full image of each blade as represented by the bottom left hand part FIG. 3, the second image sensor 26 will image a particular feature on a blade, for example its leading edge. Due to the orthogonal orientation of the line of pixels in the second image sensor 26, this will build up a composite image such that the feature appears as a sloping line L in the composite image as illustrated in the bottom right hand part of FIG. 3. At any point in time, the position of the image of the particular feature on the second image sensor 26 will be proportional to the rotational or traverse position of the blade (direction y in FIG. 3). Thus, the slope of the line L will be proportional to the speed of traverse of the blade 14. This can be used by the processor 30 in order to provide image correction to the image obtained by the first sensor 24. This effectively makes it position-invariant and therefore compensated for variations in the speed of rotation of the rotating part.

Figure 4:
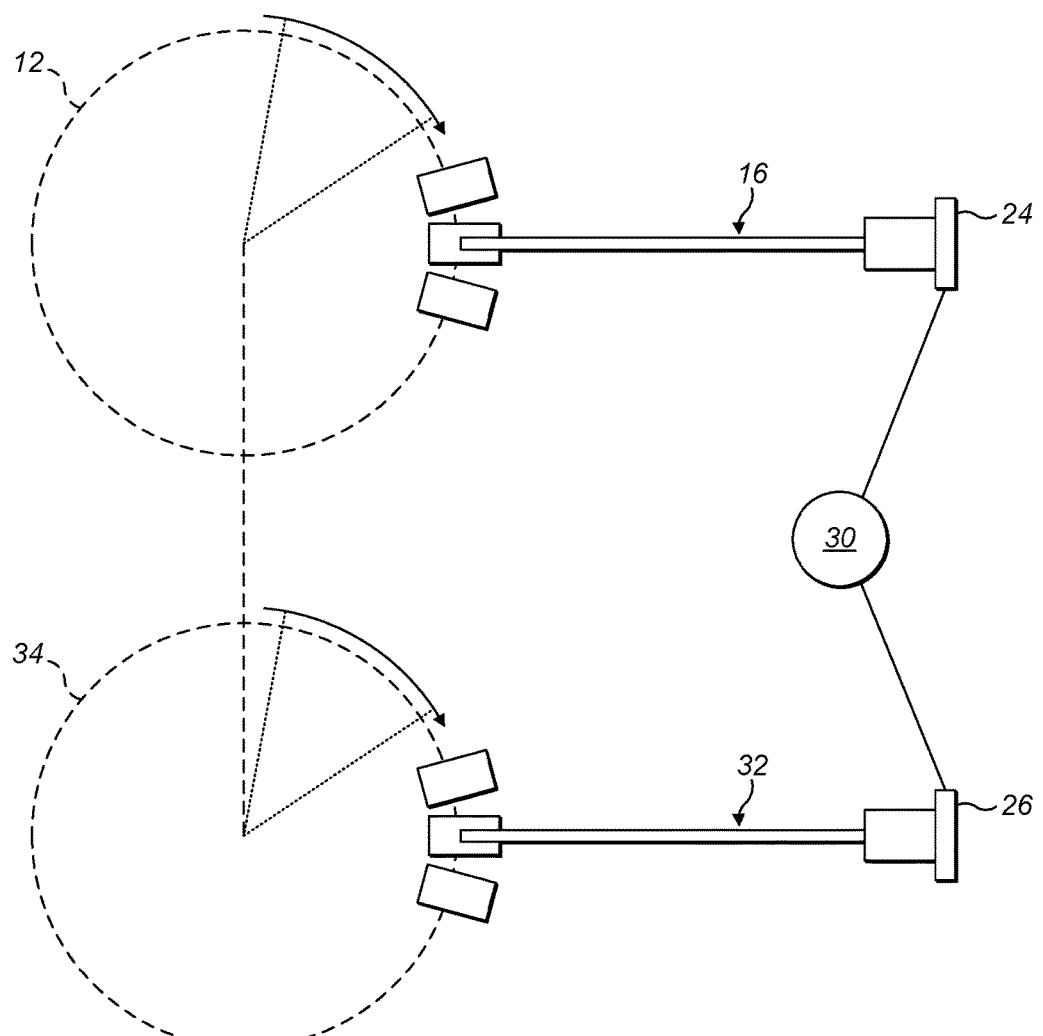
FIG. 4 is a schematic diagram of another embodiment of the invention.

As an alternative to using a single endoscope 16 and beam splitter 28, it is possible to employ a second endoscope 32 as shown in FIG. 4, which is arranged to capture an image of a different stage 34 in the engine which is mechanically linked to the first one (disc 12) being viewed by the first endoscope 16. For example, intermediate compressor stages in a gas turbine are linked. High pressure stages are also linked and turbine stages are linked. The second endoscope 32 is arranged in the same manner as the first but the second line scan image sensor 26 associated with the second endoscope (32) is arranged so that its line of pixels is orthogonal to the line of pixels in the first image sensor 24 with respect to the direction of image movement.

Using two orthogonally oriented line scan image sensors 24, 26 in this way allows for compensation for variations in speed by two possible methods. In a first method, the images from the two sensors 24, 26 are captured and stored in the processor 30. By means of a correction algorithm, the image from the second sensor 26 can be used to derive a correction factor to apply to each line of the image obtained by the first sensor 24, so as to effectively remove any image distortions caused by speed variation.

In another method, the signal from the second line scan image sensor 26, indicative of the position of the imaged feature on the sensor can be used in real time to trigger the sequential line scan image capture carried out by the first sensor 24.

In this way, the method and apparatus of the present invention provides a system for efficiently capturing an image of each blade on each stage of a gas turbine engine (or equivalent features in any other rotary system) which allows inspection to be carried out rapidly and in a more automated fashion. This decreases system downtime and hence costs associated with the inspection.

The invention claimed is:

1. A method for capturing an image of a moving object in a rotary system, comprising using a first endoscope to form an image of a first moving object and to convey the image of the first moving object to a first line scan image sensor, capturing 1-dimensional line images of the first moving object with the first line scan image sensor which is oriented to lie orthogonal to the direction of movement of the image of the first moving object past the first image sensor, and combining successive line images obtained by the first image sensor to form a composite 2-dimensional image of the first moving object, further comprising providing a second endoscope associated with a second line image scan sensor and positioning the second endoscope adjacent a second moving object in the rotary system which is mechanically linked to the first moving object, wherein the second line scan image sensor is oriented orthogonal to the first line scan image sensor, and captures an image of a particular feature of the second moving object.

2. A method as claimed in claim 1, wherein the first and second endoscopes each comprise an elongate shaft with a proximal end and a distal end and an optical system operable to form an image of an object adjacent to the distal end and transmit the image to the proximal end, the method further comprising arranging the first and second image sensors at the respective proximal ends of the elongate shafts of the first and second endoscopes to receive the image from the optical system.

3. A method as claimed in claim 1, further comprising using the image from the second image sensor to correct the composite image obtained by the first image sensor in order to compensate for variations in the speed of movement of the first object.

4. A method as claimed in claim 1, further comprising using a signal derived from a moving image feature on the second image sensor to trigger the line image capture by the first image sensor.

5. Apparatus for capturing an image of a moving object in a rotary system, comprising a first endoscope to form an image of the moving object and to convey the image to a first line scan image sensor which is oriented orthogonal to the direction of movement of the image of the object past the first image sensor and which is operable to capture 1-dimensional line images of the moving object, and a processor to combine the line images captured by the first image sensor to form a composite 2-dimensional image of the moving object, further comprising a second endoscope with a second line scan image sensor, the second endoscope arranged to view a second moving object in the rotary system which is mechanically linked to the first moving object in the rotary system, wherein the second line scan image sensor is oriented orthogonal to the first line scan image sensor to capture an image of a particular feature of the second moving object.

6. Apparatus as claimed in claim 5, wherein the first and second endoscopes each comprise an elongate shaft with a proximal end and a distal end and an optical system operable to form an image of an object adjacent the distal end and transmit the image to the proximal end and the first and second image sensors are arranged at the proximal ends of the respective shafts.

* * * * *